United States Patent [19]

Schlossman et al.

[11] Patent Number: 5,120,642

[45] Date of Patent: Jun. 9, 1992

[54] MONOCLONAL ANTIBODY WHICH DISTINGUISHES HELPER INDUCER AND SUPPRESSOR INDUCER CD4+ LYMPHOCYTES

[75] Inventors: Stuart F. Schlossman, Newton Center; Chikao Morimoto, Needham, both of Mass.

[73] Assignee: Coulter Corporation, Hialeah, Fla.

[21] Appl. No.: 442,062

[22] Filed: Nov. 28, 1989

[51] Int. Cl.$^5$ .................. C07K 15/28; C12N 5/20; G01N 33/577

[52] U.S. Cl. .................. 435/7.24; 424/1.1; 424/85.91; 435/7.9; 435/34; 435/172.2; 435/240.27; 435/948; 436/548; 530/809; 530/388.75; 530/388.73; 530/388.7; 935/110

[58] Field of Search .............. 424/1.1, 85.91; 435/7.24, 7.9, 34, 172.2, 240.27, 948; 436/548; 530/387, 389, 809; 935/110

[56] References Cited

U.S. PATENT DOCUMENTS 4,661,446 4/1987 Schlossman et al. ............. 435/7.24
4,677,056 6/1987 Dupont et al. .................... 435/7.24

OTHER PUBLICATIONS

D. A. Fox et al, *Jour. Immunol.*, 133, 1250-1256, 1984.
C. Morimoto et al, *Jour. Immunol.*, 134, 7508-1515, 3762-3769, 1985.
S. H. Smith et al, *Immunolology*, 58, 63-70, 1986.

Primary Examiner—David Saunders
Attorney, Agent, or Firm—Myron C. Cass

[57] ABSTRACT

A monoclonal antibody which binds preferentially to a subset of the human CD4+ lymphocyte population whereby to positively and precisely distinguish between helper-inducer and suppressor-inducer cells in the CD4+ cell population. The monoclonal antibody recognizes a novel antigen on the CD4+ lymphocytes by means of which it can bind CD4+ cells which express the antigen on the surface of CD4+ cells. The CD4+ subset cell population to which this antibody preferentially binds is the CD4+ helper-inducer population. This selectivity of the monoclonal antibody enables cell sorting, diagnostic and possible therapeutic applications thereof to be realized. The monoclonal antibody also reacts with CD8 cells, B cells and macrophages.

21 Claims, 3 Drawing Sheets

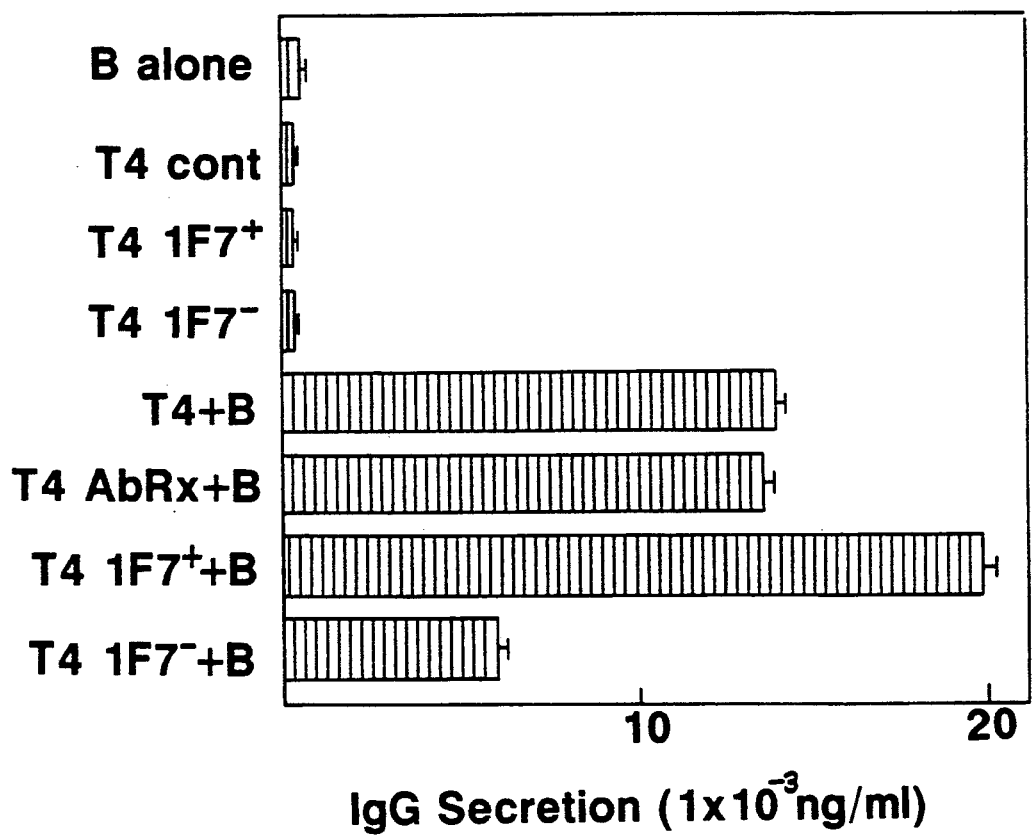
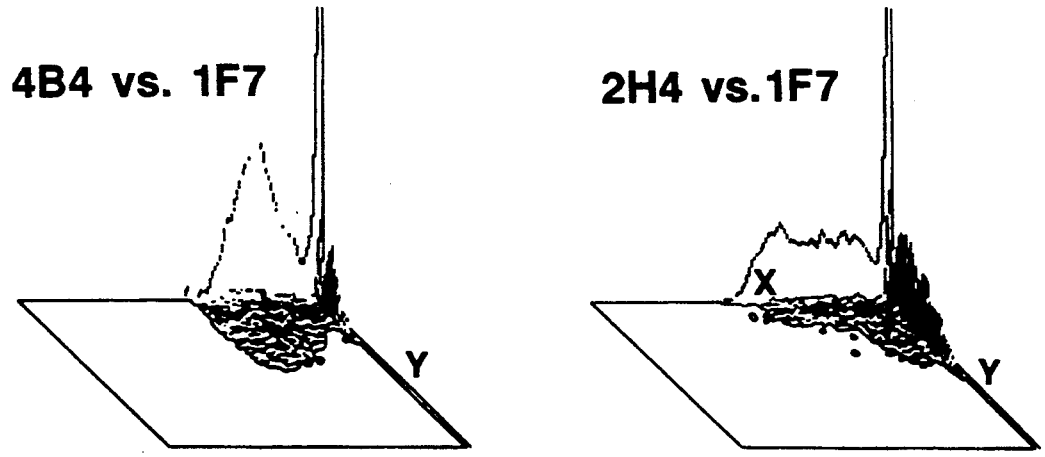

MONOCLONAL ANTIBODY WHICH DISTINGUISHES HELPER INDUCER AND SUPPRESSOR INDUCER CD4+ LYMPHOCYTES

This invention was made with Government support in part by National Institutes of Health grant Nos. Al-12069, Al-20729, CA25369 and AR 33716.

FIELD OF THE INVENTION

This invention relates to monoclonal antibodies, and more particularly, relates to a monoclonal antibody which binds to a novel cell surface antigen on lymphocytes which enables distinguishing between CD4+ helper-inducer and CD4+ suppressor-inducer cells in human CD4+ lymphocyte populations.

BACKGROUND OF THE INVENTION

Lymphocytes are white blood cells which derive from either the thymus or the bone marrow. Lymphocytes cooperate in various ways to effect immunological responses. The bone marrow-derived or B lymphocyte cells (B-cells) secrete immunoglobulins in a primary or in a secondary immune response after appropriate antigen stimulation. Thymus-derived or T lymphocyte cells (T-cells) function as effector cells in cell mediated immune reactions, cooperate with B-cells to form immunoglobulin and suppress certain B-cell functions.

Monoclonal antibody technology first set forth by Kohler and Milstein (Nature 256:495-597 [1975]) allows production of reproducible monoclonal antibodies of predefined specificity. Lymphocytes now can be divided into subsets and further subpopulations by combining flow cytometry cell sorting techniques with specific membrane monoclonal antibodies directed to surface antigens. The state of maturation of the cell and functional differentiations based upon differing membrane surface structures, known as phenotyping, serve as population markers. Population marking with monoclonal antibodies enables study of the role of various populations of lymphocytes in regulating immune response and allows better recognition of the functions of the subpopulations. Functionally relevant cell surface molecules are identified by their ability to enhance or inhibit response to various stimuli.

Several in vitro tests are available to assess lymphocyte functions using various stimuli. In one such test, lymphocytes are activated with mitogens. For example, Phytohemagglutinin (PHA) or Concanavilin A (Con A) are mitogens which can be used to activate T-cells. Pokeweed Mitogen (PWM) can be used to stimulate B-cells. Also, antigen stimulation of leukocytes can be performed in culture by using various antigens, such as, Tetanus Toxoid (TT) and mumps. Other assessment methods available include mixed lymphocyte culture (MLC) and cell-mediated lympholysis.

Two major T-cell subsets are the CD4+ (T4+) subset and the CD8+ (T8+) subset. The CD4+ subset is involved in regulatory "helper-inducer" functions and antigen recognition functions wherein antigen or antigen-presenting cells are recognized in association with class II major histocompatability antigens (MHA-II). It also plays a major role in regulating immune response. E. L. Reinherz et al., Cell:19:821 (1980); C. Morimoto and Schlossman, S. F., Keio J. Med: 36:351 (1987). The CD8+ subset is involved with suppressor/cytotoxic functions and recognizes antigen in association with class I major histocompatability antigens (MHA-I). CD8+ subpopulations of cytotoxic effector and suppressor effector cells can be distinguished by using, for example, a monoclonal antibody such as the one described in our pending U.S. patent application Ser. No. 116,514, which enjoys common ownership.

Various CD4+ subsets of lymphocytes have been identified by monoclonal antibodies. Monoclonal antibody anti-Ta$_1$ is expressed only on the T-cell lineage of cells and defines an activation antigen on T-cells. This monoclonal antibody immunoprecipitates a 105,000 dalton glycoprotein. D. A. Fox et al., J. Immunol. 133:1250 (1984). Anti-Ta$_1$ identifies a minor subset of T-cells enriched for the anamnestic response to TT and mumps. Both Ta$_1$+ and Ta$_1$− cells induce similar amounts of IgG synthesis by B-cells in the presence of PWM. D. A. Hafler et al., J. Immunol. 137:414 (1986).

The anti-2H4 monoclonal antibody identifies the CD4+CD45RA+ suppressor-inducer cell population which is capable of triggering CD8+ suppressor-effector cells. C. Morimoto et al., J. Immuno. 134:1508 (1985); C. Morimoto et al., J. Immuno. 134:3762 (1985). In in vitro tests, this cell subset fails to respond to soluble antigens such as TT and mumps, and exhibits poor helper function in PWM and antigen driven antibody production systems. However, this cell subset proliferates maximally in the autologous mixed lymphocyte reaction (AMLR), a response of T-cells to selfclass II major histocompatibility complex (MHC) antigens. Anti-2H4 (CD45RA) monoclonal antibody defines the 200,000 and 220,000 dalton isoforms of the LCA/T200 family of antigens. C. E. Rudd et al., J. Exp. Med. 166:1758 (1987). These CD45R molecules are hypothesized to be involved in generation of suppressor-inducer activity. C. Morimoto et al., J. Immuno. 137:3247 (1986); T. Takeuchi et al., Eur. J. Immuno. 117:97 (1987); C. Morimoto et al., Eur. J. Immuno. 18:731 (1988).

Monoclonal antibody anti-4B4(CDw29) or anti-UCHL-1 (CD45RO) identifies the reciprocol CD4+CDw29+ subset of cells. S. H. Smith et al., Immunology 58:63 (1986); M. Streuli et al., J. Immuno. 141:3910 (1988). The CD4+CDw29+ subset of cells thus responds maximally to recall antigen as memory T-cells and responds modestly in AMLR, but has poor suppressor-inducer activity. C. Morimoto et al., J. Immunol. 134:1508 (1985); C. Morimoto et al., J. Immunol. 134:3762 (1985). CDw29 molecules belong to the VLA/Integrin family of antigens which includes the fibronectin receptor and related structures. C. E. Rudd et al., J. Exp. Med. 166:1758 (1987); M. E. Hemler, Immuno. Today 9:109 (1988). This subset was determined to provide maximal help for B-cell immunoglobulin production. C. Morimoto et al., J. Immuno. 134:1508 (1985); C. Morimoto et al., J. Immunol. 134:3762 (1985). Also, the UHCL-1 and CDw29 antigens are proposed to be markers for memory T-cells. A. N. Abkar et al., J. Immuno. 140:2171 (1988); H. M. Serra et al., J. Immuno. 140:1435 (1988). Both UCHL-1 and CDw29 are on a high percentage of thymocytes (90% and 60%, respectively). However, this subset exhibits poor suppressor-inducer activity and responds poorly in AMLR. Both the CD4-CDw29. and CD4+CD45RA+ subsets of CD4+ cells react equally to alloantigen.

Other monoclonal antibodies capable of distinguishing T-cells and CD4+ subsets are known. These include anti-late differentiation antigen (anti-LDAl) (Suciu et al., Nature 318:465 [1985]), anti-D44 (A. Bernard et al., J. Immuno. 132:2338 [1984]; C. Calvo et al., J. Immuno. 136:1144 [1986]) and anti-Tp103 (B. Fleischer, J. Immuno. 138:1346 [1987]; B. Fleischer et al., J. Immuno. 141:1103 [1988]). However, none of these monoclonal antibodies can distinguish between two distinct functional populations, the population which responds maximally to the recall antigen and provides good helper function and the populations which cannot provide helper function or respond to the recallantigen in a population of CD4+ cells are precisely as the anti-1F7 monoclonal antibody.

Although the production of hybrid cell lines nad monoclonal antibodies is well known at this stage of implementation, great care must be exercised in the separation and maintenance of hybridoma cells insulture. Isolated clones have been known to produce antibodies against a subject antigen which differs from clone to clone since antibodies produced by different cells may react with different antigenic determinants on the same molecule. Adequate testing of the resulting antibody or antibody-containing medium, serum or ascitic fluid is essential. It is necessary to characterize the antibody of each clone which contributes to the complexity of producing monoclonal antibodies which are to be used in both diagnostic and therapeutic applications.

In developing a desied monoclonal antibody, one must identify and locate the antigenic determinant which will elicit a specific antibody to bind with it. Or, conversely, develop several hundred hybridoma clones from fusions performed and exhaustively screen them against normal and nonnormal tissue and different antigens to identify and define that clone which produces the antibody with the desired binding specificity. The object of this invention is to provide a monoclonal antibody which binds to a particular antigenic determinant expressed on the surface of human CD4+ (T4+) cells which enables such functional populations within this T-cell population to be determined. A monoclonal antibody is provided which enables a more precise phenotyping of the CD4+ population so as to distinguish between helper-inducer and suppressor-inducer populations. The CD4+1F7+ population responds maximally to recall antigen and provides good helper function, while the CD4+1F7- population cannot provide helper function or respond to the recall antigen. This monoclonal antibody also is preferentially expressed on the CD4+CDw29+ helper population, and thus can serve to subdivide further this population of cells.

The monoclonal antibody can be used in vitro to distinguish helper-inducer from suppressor-inducer CD4+ cells. The anti-1F7 monoclonal antibody can be labelled with a detectible compound so that immunological complexes can be detected. The label can comprise a dye, an enzyme, a fluorescent compound, a toxic reagent, a radioactive and electron dense element.

The monoclonal antibody also reacts with approximately 50% of CD8 cells and also reacts with B cells and macrophages. The function of such reaction of the monoclonal antibody has not been determined at this time.

SUMMARY OF THE INVENTION

A monoclonal antibody is developed which distinguishes between helper-inducer and suppressor-inducer cells in a CD4+ lymphocyte population. The surface antigen or antigenic determinant for which the monoclonal antibody is specific comprises a 110,000 dalton glycoprotein. The antigen is designated "1F7," and the monoclonal antibody appears to recognize a novel antigen on the CD4+ lymphocyte population.

The 1F7 antigen is expressed on both the CD4+ and CD8+subpopulations of lymphocytes, although the antigen is widely distributed throughout the lymphoid and hematopoeitic systems since it was recognized on unfractionated T-cells, B-cells, null cells, macrophages, tonsil cells and in various human cell lines. The 1F7 antigen also is preferentially expressed on the CD4+CDw29+ subset of cells. The anti-1F7 monoclonal antibody can be used to subdivide the CD4+ and/or the CD4+CDw29+ populations in a human peripheral blood lymphocyte sample so as to assess the functional hetergeneity of these cells.

The monoclonal antibody was produced from a hybrid cell line developed from immunization of Balb/c J mice with a stimulated T-cell line derived from the new world primate species *Aotus trivirgatus*.

BRIEF DESCRIPTION OF THE DRAWINGS

FIG. 2 is a graph developed to show the amount of PWM-driven IgG synthesis by B-cells co-cultured with unfractionated CD4+, CD4+1F7° and CD4+1F7− subpopulations.

FIGS. 3A and 3B show two-color cytofluorographic analysis of CD4 cells with anti-4B4 (CDw29) or anti-2H4 (CD45RA) antibody conjugated to phycoerythrin, and anti-1F7 antibody (followed by FITC anti-mouse Ig) performed on a logarithmic scale. The fluorescence intensities of 4B4 or 2H4 and 1F7 are expressed on the X and Y axis and the vertical axis shows cell number.

DESCRIPTION OF THE PREFERRED EMBODIMENTS

Monoclonal Antibody Development

Figure 1A:
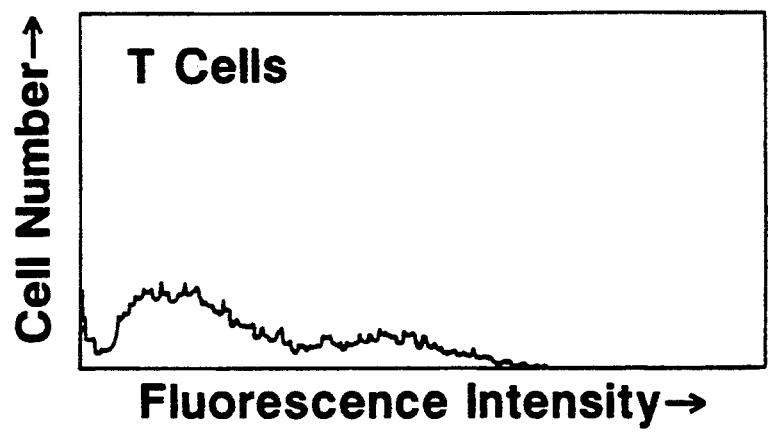
FIGS. 1A–1C are fluorescence graphs showing the reactivity of unfractionated T cells (FIG. 1A), CD4+ cells (FIG. 1B) and CD8+ cells (FIG. 1C) with anti-1F7 monoclonal antibody. Analysis was performed by using a logarithmic scale. Fluorescence intensity is represented on the horizontal axis, and cell number is represented on the vertical axis.

Balb/c J mice were immunized with cells of a PHA-stimulated T-cell line derived from the new world primate species *Aotus trivirgatus* using standard hybridoma procedures. The mouse splenocytes were harvested and fused with the myeloma cell line NS-1. The cell population was cultured in Hypoxanthine-aminopterin-thymidine (HAT) medium to obtain hybridoma cells to be cloned. Hybridoma cultures containing antibodies reactive with human T-cells were selected. Cloning and recloning of hybridoma cultures containing monoclonal antibodies reactive with human T-cells were performed by limiting dilution methods in the presence of feeder cells. Malignant asoites then were developed and used for analysis.

The isotype of the monoclonal antibody embodying the invention was determined to be mouse isotype IgG1 by staining with fluorescein-labelled goat anti-mouse IgG1 and failure to stain with fluorescein-labelled antibodies directed against other subclasses of mouse Ig.

The reactivity of monoclonal antibody anti-1F7 with lymphoid cells and human cell lines was determined. Human peripheral blood mononuclear cells were isolated from healthy donors by Ficoll-Hypaque ® (Pharmacia) density gradient centrifugation. Unfractionated mononuclear cells were depleted of macrophages by adherence to plastic, as described in C. Morimoto et al., J. Immunol. 134:1508 (1985). Cells that adhered to plastic were recovered and used as a macrophage-enriched population by the procedures described in C. Morimoto et al., ibid.

The macrophage-depleted mononuclear cells next were separated into erythrocyte rosette positive (E+) and erythrocyte rosette negative (E-) populations with 5% sheep erythrocytes as described in C. Morimoto et al., ibid. The E+ population fractions were divided into CD4+ and CD8+ cell populations by treating with anti-CD4 or anti-CD8 monoclonal antibody and rabbit complement as described in C. Morimoto et al., ibid and C. Morimoto et al., J. Immunol. 134:3762 (1985). After lysis with anti-CD4 and complement, greater than 90% of the residual cells were found to be CD8. cells, and less than 5% were found to be CD4+ cells ("CD8+ cells"). After lysis with anti-CD8 and complement, greater than 90% of the cells were determined to be CD4+ cells, and less than 5% were determined to be CD8+ cells ("CD4+ cells"). The E-population was fractionated further into B-cell and null cell populations by complement-mediated lysis with anti-Mol and anti-BI. respectfully, as described in R. F. Todd et al., J. Immunol. 126:1435 (1981) and L. M. Nadler et al., J. Clin. Invest. 67:134 (1981). Suspensions of human thymocytes were produced from fragments of thymus obtained at cardiac surgery from infants aged 2 months to 4 years.

These cell populations were reacted with monoclonal antibody and analyzed by cell sorting procedures using an EPICS ® V cell sorter instrument marketed by Coulter Corporation of Hialeah, Florida. The monoclonal antibody embodying the invention was determined after analysis for reactivity with unfractionated T, CD4 and CD8 cells and characterized as reactive with both CD4 and CD8 cells and binding specifically to the antigen identified herein as "1F7." The monoclonal antibody anti-1F7 can distinguish between helper-inducer and suppressor-inducer cells in CD4+ lymphocyte populations. The anti-1F7 monoclonal antibody defines a cell surface structure which comprises a 110,000 dalton molecular weight glycoprotein. Sequential immunoprecipitation studies and two dimensional gel analysis, as will be fully discussed, indicate that the 1F7 monoclonal antibody recognizes a novel antigen on CD4+ cells.

Reactivity of anti-1F7 with unfractionated T, CD4 and CD8 cells

Figure 1B:
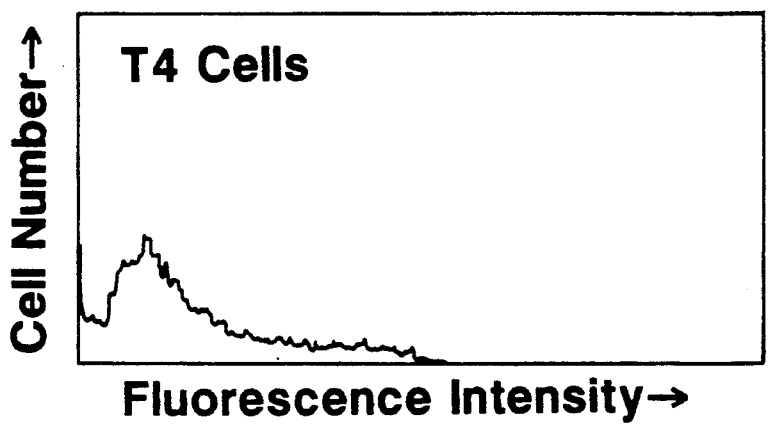
Figure 1C:
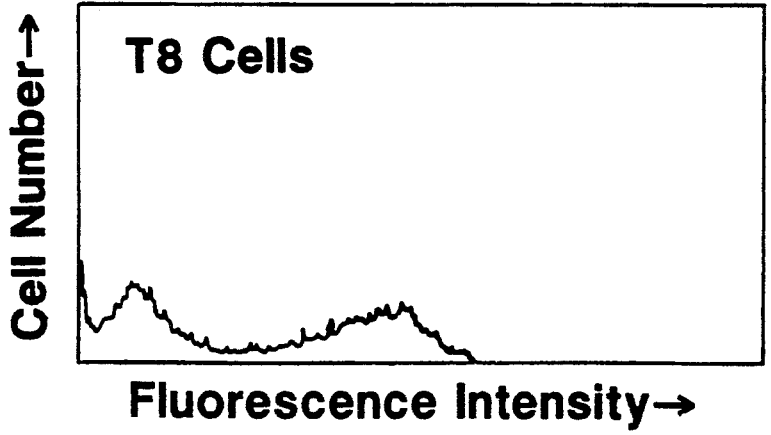

The reactivity of anti-1F7 monoclonal antibody with unfractionated T-cells, CD4+ lymphocytes and CD8+ lymphocytes was determined using an EPICS ® V cell sorter commercially available from Coulter Corporation, Hialeah, Florida. The data are shown in FIG. 1. Two peaks, one of low fluorescence and the other of high fluorescence, were seen in each population. 1F7 was expressed on $57\pm4\%$ unfractionated T-cells, $62\%\pm4\%$ of CD4+ cells and $54\%+3\%$ of CD8+ cells. Thus, 1F7 T-cells were found in both the CD8+ and CD4+ sub-population of cells. Although the anti-1F7 monoclonal antibody also reacted with CD8+ cells, the data collected focused on the subsets of CD4 cells.

Proliferative Response of Unfractionated CD4, CD4+1F7+ and CD4+1F7− lymphocytes

Since anti-1F7 was found to be reactive with approximately 60% of the CD4+ peripheral blood lymphocytes (PBL), it was used to subdivide the CD4+ population to assess the functional heterogeneity of these cells. Of the two peaks, one of high fluorescence and the other of low fluorescence, only the high fluorescence peak was selected and further tested. Thus, the population of low fluorescence was excluded. This high fluorescence population comprised approximately 40% of the total CD4+1F7+ cell population. Cytofluorographic analysis was performed by indirect immunofluorescence using fluorescein-conjugated F(ab')$_2$ goat anti-mouse F(ab')$_2$ on an EPICS ® V cell sorter. Background fluorescence was determined with control ascites obtained from mice immunized with non-secreting hybridoma clones. All monoclonal antibodies were used in antibody excess at dilutions of 1:250 to 1:1000.

CD4+ cells were separated into 1F7+ and 1F7− populations. $80\times10^6$ CD4+ cells were cultured overnight, labelled with 8 ml of a 1:300 dilution of anti-1F7 ascites fluid and the reaction was developed with fluoresce-inconjugated F(ab')$_2$ goat anti-mouse Ig. Cells were separated into CD4+1F7+ and CD4+1F7− cell populations using an EPICS ® V cell sorter as described in C. Morimoto et al., J. Immunol. 135:1508 (1985) and C. Morimoto et al., J. Immunol. 134:3762 (1985). CD4+ cells were separated further into CD4+4B4+1F7+ and CD4+4B4+1F7− populations by using anti-4B4 monoclonal antibody conjugated with phycoerythrin (PE) and anti-1F7 monoclonal antibody conjugated with fluorescein isothiocyanate (FITC). In all instances, post sort viability and purity of separated T-cell subsets was in excess of 95%.

The in vitro proliferation response of T-cells and separated lymphocytes to mitogens, soluble antigens, alloantigens and autoantigens were tested in triplicate in round bottom microtiter culture wells using an 0.2 ml volume of cells in standard RPMI 1640 culture medium supplemented with 10% human AB serum, 2 mM L-glutamine, 25 mM HEPES buffer, 0.5% sodium bicarbonate and 1% penicillin-streptomycin as described in C. Morimoto et al., J. Immuno. 134:1508 (1985). Macrophages at 5% final concentration were added to all lymphocyte populations at initiation of in vitro culture. PHA and Con A stimulated cultures were pulsed after four days with 1 $\mu$Ci of tritiated thymidine [$^3$H]TdR (1.9 ci/mM sp. act.) per well. Soluble and cell surface antigen stimulated cultures were pulsed after six days. Monoclonal antibodies as ascites or in purified forms were included as controls. The wells were incubated for 18 hours. Cells then were harvested with a Mash II apparatus and [$^3$H]TdR incorporation was measured on a Packard scintillation counter (Packard Inst. Co.).

The proliferative responses of unfractionated CD4+ cells, CD4+1F7+ and CD4+1F7− lymphocytes was determined. Tritium incorporation in response to soluble antigens TT and mumps was determined to be over 10-fold and 20-fold greater, respectively, in the 1F7+ population than those in the 1F7-population. These differences were determined to be significant ($p<0.001$). However, tritium incorporation in response to relatively higher doses of Con A (at 50 $\mu$g/ml) and in AMLR was higher in the 1F7- population than in the 1F7+ population ($p<0.05$). Thus, these proliferative assays showed that CD4+1F7+ cells were highly responsive to recall antigens, such as, TT or mumps, while CD4+1F7− cells were more responsive to Con A and autologous antigens.

Detection of In Vitro IgG Secretion

Data was developed to determine whether T-cell help for B-cell immunoglobulin production was restricted to the CD4+1F7+ or the CD4,1F7− cell population. Unfractionated CD4+ cells, CD4+1F7+ cells or CD4+1F7− cells were cultured in round bottom microtiter culture plates at 37° C. in a humidified atmosphere with 5% $CO_2$ for 7 days in RPMI 1640 which was supplemented with 20% heat inactivated fetal calf serum, 0.5% sodium bicarbonate, 4 mM L-glutamine, 25 mM HEPES buffer and 1% penicillin-streptomycin. Various numbers of unfractionated CD4+ or purified CD4+1F7+ and CD4+1F7− T-cell subsets were mixed with $5 \times 10^4$ B-cells in a 0.1 ml volume. Then, 0.1 ml of PWM at a 1:100 dilution was added to the cells. Macrophages were added to all populations at a 5% final concentration at initiation of in vitro cultures. Sometimes, various concentrations of CD8+ cells were added to a mixture containing $2 \times 10^4$ CD4+ cells and $5 \times 10^4$ B-cells with PWM. Monoclonal antibodies as ascites or in purified forms were included to determine the effect of the antibody on PWM-driven IgG synthesis. Cultures were terminated at day 7, at which time the supernatants were harvested and the amount of IgG secretion into the supernatant fluid was determined by solid phase radioimmunoassay as described in C. Morimoto et al., J. Clin. Invest. 67:753 (1981); C. Morimoto et al., J. Immunol. 134:1508 (1985).

The data developed by these tests are graphically displayed in FIG. 2. It was determined that neither B-cells, unfractionated CD4+ cells nor sorted CD4+ cell subsets secreted IgG when cultured alone. However when unfractionated CD4+ cells and B-cells were mixed together and incubated with PWM, 14,240±510 ng of IgG per ml of culture supernatant were secreted. CD4+ cells treated with antiIF7 and FITC-labelled goat anti-mouse IgG had no effect on the help these cells provided to B-cells.

CD4+1F7+ and CD4+ 1F7− cells were added in equal numbers to separate cultures of autologous B-cells. It was determined that the IgG secretion induced by CD4+1F7+ population, 19,960±750 ng, was approximately three (3) times greater than that obtained in the B-cell and CD4+1F7+ combination, 6,120±410 ng. It also was determined in a quantitative comparison study that the helper function provided by the CD4+1F7+ cells was always two to four times greater than that of CD4+1F7− cells at any given number of T-cells and B-cells tested. Thus, the majority of helper activity for antibody production by B-cells in response to PWM was found within the CD4+1F7+ subset of CD4+ cells, although the CD4+1F7− cells did provide some helper effect.

Effect of CD4+1F7+ or CD4+1F7− cells on the Generation of Suppressor-Effector Cells It next was determined whether CD4+1F7+ and CD4+1F7− cells could induce suppression of IgG production in vitro. Varying numbers of CD8+ cells were added to constant concentrations of B-cells (5 x 104) in the presence of PWM. Then, fractionated CD4+1F7− or CD4+1F7− cells were added. Suppression of IgG production was calculated as follows:

Control IqG - IgG observed by addn. of CD8+ cells×100 Control IgG Production

Marked suppression in IgG production was observed when increasing numbers of CD8+ cells were added to B-cells in the presence of CD4+1F7− cells. It also was determined that only slight suppression of PWM driven IgG synthesis occurred when moderate or low numbers of CD8+ cells were added to B-cells in the presence of CD4+1F7+ cells. These results indicate that the CD4+1F7− cells are more efficient than CD4+1F7− cells in the induction of the CD8+ cell suppression of IgG production.

Relationship Between CD45R, CDw29 and 1F7 Antigens on CD4+ Cells

It previously was determined that the CD4+CD45R+ subset of cells provided poor helper function in PWM-driven and antigen-driven antibody production systems, failed to respond to soluble antigens but responded maximally to self-class II antigen in the AMLR. C. Morimoto et al., J. Immunol. 134:1508 (1985). It also was determined that this subset of cells had suppressor-inducer activity which triggered CD8+ (T8+) suppressor cells, as well as, provided maximal helper function for B-cell Ig synthesis but had poor suppressor-inducer activity. C. Morimoto et al., J. Immuno. 134:3762 (1985). Further, the CD4+CDw29− subset responded maximally to soluble antigens but responded poorly in the AMLR. These results suggested that the CD4+1F7− subset of cells corresponded to the CD4+CDw29+ subset of cells and that the CD4+1F7− subset of cells corresponded to the CD4+CD45R+ subset of cells.

The relationship between CD45R, CDw29 and 1F7 antigens on CD4+ cells therefore was studied by using double fluorescence staining with anti-CD45R PE conjugate, anti-CDw29 PE conjugate and anti-1F7 FITC conjugate. These results are shown in FIGS. 3A and 3B. Of the 1F7+ cells, the majority (>80%) expressed CDw29 antigen. These results indicate that CD4+1F7+ cells substantially overlap CDw29+ subset of CD4+ cells. Also, additional studies of PBL from 10 different donors determined that 60–75% of the CD4+ cells expressing the CDw29 antigen expressed the 1F7 antigen. Thus, it was determined that anti-1F7 monoclonal antibody could be used to subdivide the CDw29+ cell subset. Additionally, although antigen density was low, 30% of cells expressing the CD45R (2H4) antigen co-expressed 1F7. Virtually no CD4+ cells expressed both CD45R and 1F7 at high antigen densities.

Proliferative Response of CD4+CDw29+1F7+ and CD4+CDw29+1F7− Subsets

Further experiments were conducted to evaluate the functional heterogeneity of 1F7+ and 1F7− populations of the CD4+CDw29+ subset of cells by examining proliferative responses of the CD4+CDw29+1F7+ and CD4+CDw29+1F7− populations of the CD4+CDw29+ subset of cells following antigenic stimulation. Anti-CDw29 PE and anti-1F7 FITC were used in conjunction with an EPICS ® V cell sorter to separate cells into CD4+CDw29+1F7+ and CD4+CDw29+1F7− subsets. Both postsort variability and T-cell subset purity was found to be in excess of 95%.

It was determined that the CD4+CDw29+1F7+ population responded maximally to TT, whereas the CD4+CDw29+1F7− population responded poorly to TT. The CD4+CDw29+1F7+ and the CD4+CDw29+1F7− subsets responded almost equally to alloantigen. These results indicate that the CD4+CDw29+1F7+ but not the CD4+CDw29+1F7− subset of cells is the population of cells which maximally responds to soluble antigen such as TT.

PWM-Driven IgG Synthesis by B-Cells

Experiments were conducted to determined whether T-cell help for B-cell Ig synthesis was restricted to the CD4+4B4+1F7+ subset of cells by quantitatively comparing the helper function provided by the CD4+CDw29+1F7+ and CD4+CDw29+IF7− T-cells for B-cell Ig synthesis. It was determined that both subsets provided almost equal help for PWM-driven B-cell IgG synthesis, although the degree of help provided by these populations seemed to vary between donors.

Effect of anti-1F7 Monoclonal Antibody on Proliferative Response of CD4+ Cells Data was developed to determined whether the IF7 molecule itself was involved in lymphocyte activation by examining the effect of anti-1F7 monoclonal antibody on mitogen and soluble antigen stimulated T-cell proliferation. It was determined that the anti-1F7 monoclonal antibody caused a 62-70% inhibition of proliferation in response to TT whereas the proliferative response of CD4+ cells to PHA and Con A was inhibited only slightly. However, anti-1F7 monoclonal antibody inhibited TT induced proliferation only slightly in 2 of 13 donors exhibiting only 11-20% inhibition of this response. Only minimal effects were observed on these proliferative responses when control antibodies of the same IgG1 isotype and saturated concentration (anti-TQl and anti-CD4) were added to the cultures. However, it has been shown that anti-CD4 antibody of this concentration inhibits AMLR response by 70-80%. T. Takeuchi et al., J. Immuno. 139:665 (1987). These results suggest either that the IF7 molecule itself is involved in the soluble antigen-stimulated T-cell response, or, the results may reflect an association of the IF7 antigen with other molecules involved in that response.

Effect of Anti-1F7 Monoclonal Antibody on PWM-Driven IgG Synthesis

Next, experiments were performed to assess the role of the IF7 molecule in the generation of helper signals for B-cell Ig synthesis by adding anti-1F7 monoclonal antibody to the culture system and determining whether inhibition of the PWM driven IgG synthesis occurred. The percent suppression was calculated as follows:

$$\frac{\text{Control } IgG \text{ response} - \text{Observed } IgG \text{ Response}}{\text{Control } IgG \text{ response}} \times 100$$

Marked inhibition of PWM driven IgG synthesis was observed regardless of the cell combinations studied when anti-1F7 was added to the cultures. However, when control antibodies of the same IgG1 isotype, such as, anti-TQ$_l$, anti-CD4 and anti-CDw29, were added to the culture systems, no or slight inhibition of PWM-driven Ig synthesis resulted. The data therefore suggests that the mechanism of inhibition of PWM-driven IgG synthesis was not due to the activation of CD8+ suppressor cells, because PWM-driven synthesis by the mixture of B-cells and CD4+CDw29+ cells was not inhibited by the addition of anti-1F7 to the cultures.

Isolated B lymphocytes were cultured in RPMI 1640 medium containing 15% fetal calf serum, 4 mM glutamine and Gentamicin at 50 μg/ml in 96-well round bottomed microtiter plates containing 200 μl of media per well. Epstein-Barr Virus (EBV) was used as the supernatant fluid of cultures of marmoset cell line B95-8 and was added to cultures at a final concentration of 10% (v/v%) as described in A. Forsgren et al., cell Immunol. 112:78 (1988). It was determined that anti-1F7 monoclonal antibody did not inhibit B-cell differentiation into antibody secreting cells in this EBV-activated B-cell differentiation assay. These data suggest that the IF7 molecule may be involved in helper CD4 and B-cell interactions. However, anti-1F7 inhibited PWM-driven IgG synthesis an average of 15% in 3 of 19 donors.

Immunoprecipitation Studies

For one-dimensional SDS-PAGE and sequential depletion studies, T-cells were stimulated with Con A (20 μg/ml) for 2-5 days and then resuspended in 5% α-D-mannopyranoside in RPMI 1640, washed in phosphate buffered saline (PBS) and sequent labelled by lactoperoxidase-catalysed iodination. For NEPHGE (non-equilibrium gel electrophoresis)/SDS-PAGE, a H9 T-cell line was labelled by the same method. Labelled cells next were washed twice in PBS and solubilized in lysis buffer (1% w/v nonidet, P-40 in 10 mM Tris-HCl buffer, pH 8.2, containing 150 mM NaCl and 1 mM phenyl methyl sulfonyl fluoride [PMSF]) as described in C. E. Rudd et al., J. Exp. Med. 166:1758 (1987). Then, cell lysates at approximately $5 \times 10^7$ cells/ml were precleared overnight with 50 μl of 10% Staphylococcal Protein A (SAC) and/or protein A Sepharose (Pharmacia). The lysate then was incubated for 1 hour with 10 μg of the appropriate antibody and 3 μl of rabbit antimouse Ig (Dako Corp., Santa Barbara, CA) followed by precipitation with 50 μl of a 10% solution of protein A-Sepharose. Some immunoprecipitations used antibodies directly coupled to protein-A agarose as described in C. Schneider et al , J. Biol. Chem. 257:10766 (1982). Immune complexes were washed at 4° C. once with lysis buffer containing 500 mM NaCl, once with lysis buffer containing 0.1% sodium dodecyl sulfate (SDS) and once with lysis buffer alone; some immune complexes were washed four times with only lysis buffer. Immunoprecipitates were eluted by boiling 5 minutes in 50 μl SDS sample buffer (0.1M Tris-HCl, pH 6.8 containing 10% v/v glycerol and 1% SDS). The sample beads were loaded and run on 7.5% polyacrylamide gels or gradient gels (5-7.5%) as described in U. K. Laemmli, Nature 227:680 (1970).

When immunoprecipitations involved sequential depletions, lysates were precleared by five (5) to six (6) successive immunoprecipitations with the first antibody, and then precipitated one time each with the second and third antibodies.

NEPHGE/SDS-PAGE was performed using an ampholine range of pH 4.0-9.0 as described in P. H. O'Farrell, J. Biol. Chem. 250:4007 (1975). The gels then were fixed and dehydrated using a gel dryer. Radioactivity was detected by exposing Kodak X-R5 film (Eastman Kodak Co., Rochester, NY) at −70° C. with intensifying screen (Cronex Lightning Plus, DuPont-New England Nuclear, Wilmington, DE).

Immunoprecipitation studies were performed to determine whether the IF7 molecule was similar or distinct from the CDw29 and UCHL-1 molecules. The UCHL-1 epitope previously was reported to be expressed on a subset of T4 cells similar to the CDw29 subset in the peripheral T-cell compartment. S. H. Smith et al., Immunol. 58:63 (1986).

Immunoprecipitates from lysates of iodinated Con A-stimulated peripheral blood T-cells were compared. The anti-IF7 monoclonal antibody precipitated a prominent diffuse band at 110,000 daltons from peripheral T-cells. Additional bands of about 40,000 and 70,000 daltons were occassionally seen. Further, at times the material in the 110,000 dalton range focused as an extended diffuse band between 160,000 to 110,000 daltons. The biochemical basis for this variation has not been established. The anti-4B4 (CDw29) monoclonal antibody reacted with a series of bands at 135,000, 160,000 and 185,000 daltons. This structure recently was shown to be a member of the integrin family of adhesion molecules. C. E. Rudd et al., J. Exp. Med. 166:1758 (1987); C. E. Rudd et al., Proc. Natl. Acad. Sci. USA 85:5190 (1988). The anti-UCHL-1 monoclonal antibody precipitated a single chain of 180,000 daltons. This antigen was found to react with the lowest $M_r$ isoform of the LCA/T200 antigen. (Beverley P. C., Immunol Lett. 14=263 (1987).

Anti-$Ta_1$ has been described as recognizing a surface antigen found on activated T-cells with a molecular weight of 105,000 daltons. D. A. Fox, J. Immunol. 133:1250 (1984). Immunoprecipitation studies were performed to determine whether the broad 110,000 dalton band recognized by anti-IF7 monoclonal antibody was related to the 105,000 band recognized by anti-$Ta_1$ monoclonal antibody.

The IF7 and $Ta_1$ monoclonal antibodies precipitated a comigrating broad band at about 110,000 daltons. The equivalency of this band then was tested by sequentially depleting iodinated lysates of IF7-precipitable material, followed by immunoprecipitation with anti-$Ta_1$, which then was followed by precipitation with an unrelated antibody. Anti-IF7 precipitated the broad 110,000 dalton band which was no longer visible after preclearing by repeated immunoprecipitations with anti-IF7. Significantly, anti-$Ta_1$ also failed to precipitate visible material after preclearing with anti-IF7. Sequential precipitation of unrelated antibody, anti-class I (W6/32), was effective in precipitation of its 45,000 dalton antigen.

Mixed results were obtained when the converse sequential depletion study was performed using anti-$Ta_1$ to preclear followed by anti-IF7. Preclearing with anti-$Ta_1$ was not effective in removing all IF7-precipitable material. This indicates that anti-IF7 may precipitate additional 110,000 dalton material not precipitated by anti-$Ta_1$. This may be due to heterogeneity in the 110,000 dalton material or failure to fully preclear with the anti-$Ta_1$ antibody.

Figure 4A:
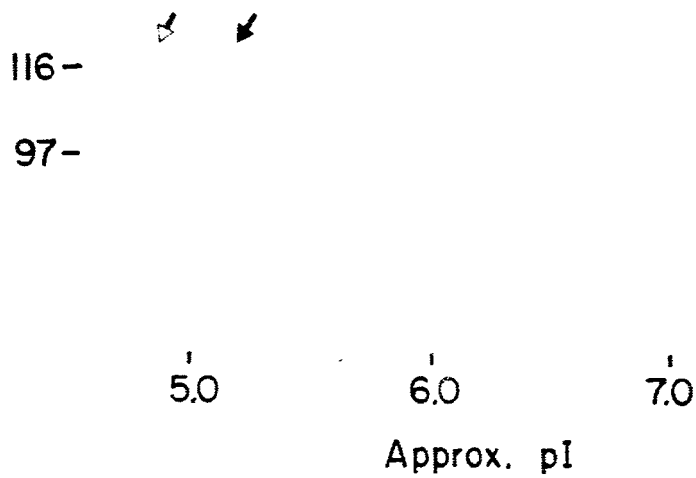
FIG. 4 shows the two-dimensional NEPHGE/SDS-PAGE of the 1F7 (A) and Ta$_1$ (B) antigens.
Figure 4B:
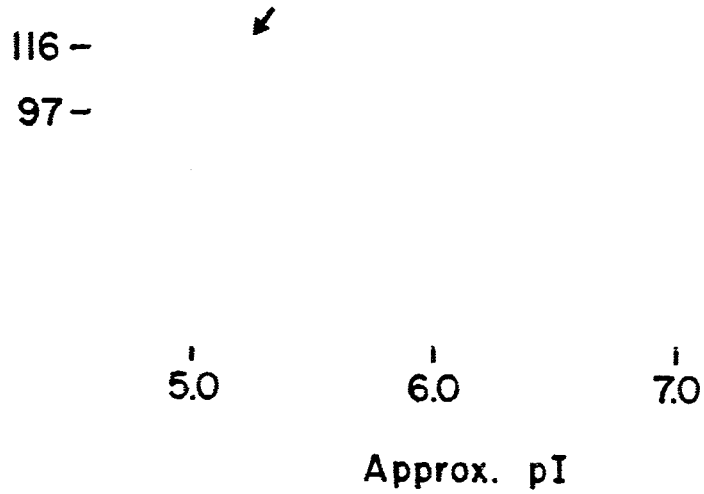

To resolve these issues, two-dimensional NEPHGE/SDS-PAGE was performed to compare the structure recognized by anti-IF7 and anti-Ta1 monoclonal antibodies. As shown in FIG. 4, the principle molecule precipitated by anti-IF7 and anti-$Ta_1$ shared identical molecular weight of 110,000 daltons and pI values between 5.2 and 5.5. However, the anti-IF7 antibody, unlike the anti-$Ta_1$ antibody, precipitated another acidic structure which shared similar molecular weight yet had different pI values between 4.5 and 4.9.

Comparative Analysis of IF7 and $Ta_1$ on Human Lymphoid and Cell Lines

TABLE 1

Reactivity of anti-1F7 and anti-$Ta_1$ antibody with human lymphoid and cell lines

| CELLS | IF7 | $Ta_1$ |
|---|---|---|
| I. Lymphoid cells | | |
| B-cells | + | − |
| Null cells | + | − |
| Macrophages | + | − |
| Tonsil cells | + | − |
| II. Thymocytes | ± | ± |
| III. T cell lines | | |
| HSB | + | + |
| H9 | + | + |
| HPB | − | − |
| Hut 78 | + | − |
| CEM | − | − |
| JM | − | − |
| Molt 4 | ± | − |
| IV. B cell lines | | |
| Daudi | + | − |
| Laz 156 | + | − ~ ± |
| Laz 509 | + | − ~ ± |
| Ramos | + | − |
| Raji | + | − |
| V. Hematopoietic lines | | |
| U-937 | ± | − |
| K-562 | − | − |
| KGl | ± | − |

Reactivity of anti-1F7 antibody determined by indirect immunofluorescence on cytofluorograph:
(−) indicates 5% reactivity background:
(±) indicates 5–30% reactivity;
(+) indicates 30% reactivity.

The reactivity of anti-IF7 and anti-$Ta_1$ monoclonal antibodies was determined by indirect fluorescence on a cytofluorograph and reactivity was graded as follows: (−) if the background was 5% or less reactive, (±) if the reactivity was 5–30%, and (+) if the reactivity was 30% or greater. As seen in TABLE 1, the anti-IF7 monoclonal antibody reacted with over 30% of peripheral B-cells, null cells, macrophages and tonsil cells, although reactivity was present in low antigen density. Thymocytes were slightly reactive (between 5–30% reactivity) with anti-IF7.

Numerous human cells lines also were tested for reactivity with anti-IF7. These data are shown in TABLE 1. It was determined that anti-IF7 was strongly reactive with 2 of 5 human T-cell lines tested (HSB, Hut 78) and weakly reactive with the Molt 4 cell line. The two lymphoblastoid B-cell lines and the three Burkitt's lymphoma lines were reactive. Of the three hematopoietic cell lines tested, KG-1 was reactive and U-937 was slightly reactive. All other human cell lines tested were unreactive.

Although the anti-IF7 and anti-Ta1 monoclonal antibodies immunoprecipitated the same structure, their reactivity with functionally distinct cell subsets differs. The data displayed in FIG. 1 and TABLE 1 show that anti-$Ta_1$ monoclonal antibody was unreactive with peripheral B-cells, null cells, macrophages and tonsil cells. Both antibodies were slightly reactive with thymic thymocytes, and were especially reactive with medullary thymocytes (high CD3+thymocytes). Anti-IF7 was reactive with 3 of 7 human T cell lines, while anti-$Ta_1$ was reactive with only 2 of 7. Anti-IF7 was reactive with all 5 B-cell lines tested and 1 of 3 hematopoietic cell lines tested, while anti-Ta1 was unreactive with the B-cell lines and hematopoietic cell lines except EBV-transformed B-cell lines (Laz156 and Laz509) with which it was somewhat reactive. Thus, while anti-IF7 was not restricted to cells of the T-cell lineage, anti-Ta$_1$ was T-cell restricted except for the slight reactivity to EBV-transformed B cell lines. Although Ta$_l$+T-cells reported to be enriched for memory T-cells responded to soluble antigen (D. A. Hafler et al., J. Immuno. 137:414 [1986]), the results of PWM-driven IgG synthesis and auto-MLR response by Ta$_l$+ and Ta$_1$- T cells are different from the present results obtained by IF7+ subsets of CD4+ cells. One possible explanation for this may be that the Ta$_1$ studies were performed with whole-T cells but not CD4 cells. Also, because the Ta$_l$+ population is smaller than the IF7+ population, these populations differ from each other. Further, anti-Ta$_l$ has no inhibitory effect on soluble antigen-stimulated T-cell responses as well as PWM driven IgG synthesis. D. A. Fox et al., J. Immuno. 133:1250 (1984).

Cross-Blocking Studies With Anti-IF7 and anti-Ta$_1$

Cross-blocking studies were performed between anti-IF7 and anti-Ta$_1$ in order to determine the relationships between the two antigens identified by the monoclonal antibodies. T-cells were 68% positive when stained with anti-IF7 conjugated to FITC. However, T-cells were 36% positive when stained with anti-Ta$_1$ conjugated to FITC. It was determined that cells preincubated with anti-IF7 (1:100 ascites) showed complete blocking of staining with anti-Ta$_1$-FITC. In contrast, cells preincubated with anti-Ta$_1$ (1:100 ascites) demonstrated only slight dropping of anti-IF staining (63%). These results, as well as the SDS gel data described, suggest that although the Ta1 molecule was recognized by anti-IF7 monoclonal antibody, the IF7 family structures also included molecules distinct from Ta$_1$.

Deposit

A culture of hybridoma cells which produce the anti-IF7 monoclonal antibody has been deposited as of Nov. 21, 1989, with the American Type Culture Collection, 12301 Parklawn Drive, Rockville, Maryland 20852, and assigned A.T.C.C. No. HB 10297.

The anti-IF7 monoclonal antibody therefore is a novel monoclonal antibody which can subdivide the CD4+ cells into two distinct functional populations, CD4+ helper inducer cells (CD4+IF7+) and CD4+ suppressor inducer cells (CD4+IF7-), whose subsets of CD4 cells have been described previously by anti-CD45R, anti-CDw29 and anti-UCHL1.

The CD4+IF7+ cells are the major subpopulation of inducer cells to proliferate in response to TT and mumps antigen and provide help for B-cell IgG synthesis. This subpopulation corresponds to the CD4+CDw29+ (CD45R−) and CD4*UCHL-1+ subsets of cells. By contrast, the CD4+IF7− cells, like the CD4+CD45R+ subset of cells, is the predominant inducer of suppressor cells and the major cell subset responding to Con A and AMLR. Further, the anti-IF7 monoclonal antibody reacted with 60–75% of the CD4+CDw29+ cell subset and thus is capable of further subdividing the CD4+CDw29+ cells into CD4+CDw29+IF7+ and CD4+CDw29+IF7- subsets of cells. The CD4+CDw29+IF7+ cell subset is the population which maximally responds to recall antigen such as TT and mumps, although helper function for PWM-driven B cell IgG synthesis belonged to both CD4+CDw29+IF7+ and CD4+CDw29+IF7− subsets. The above results strongly suggest that the CD4+ IF7+ cells appear to include memory cells.

The specificity of the IF7 monoclonal antibody within the class of CD4. cells is particularly unique and useful in view of the heretofore less precise phenotypic means available to distinguish helper inducer from suppressor inducer cells within the CD4 class of lymphocytes.

The complete diagnostic and possible therapeutic applications of the monoclonal antibody embodying the invention have not been determined.

We claim:

1. A hybrid cell line derived by hybridoma technique which produces a monoclonal antibody that binds to a common antigen comprised of a 110,000 dalton molecular weight glycoprotein on human CD4 and CD8 lymphocytes, which antigen, present on helper inducer cells but not suppressor inducer cells, enables the monoclonal antibody to distinguish between helper inducer and suppressor inducer cells in human CD4 lymphocyte populations.

2. The cell line according to claim 1 in which monoclonal antibody also binds to said common antigen on B cells and macrophages.

3. The hybrid cell line according to claim 1 which has the identifying characteristics of the cell line on deposit with the A.T.C.C., Rockville, Maryland and assigned A.T.C.C. deposit No. HB 10297.

4. A hybrid cell line derived by hybridoma technique which produces a monoclonal antibody which binds specifically to an antigen identified as the IF7 antigen on human CD4 helper inducer lymphocytes and which enables the monoclonal antibody to distinguish between helper inducer and suppressor inducer cells in human CD4 lymphocyte populations.

5. The cell line according to claim 4 which produces mouse IgG1 isotype antibody to IF7 antigen.

6. A monoclonal antibody which specially binds to a common antigen identified as the IF7antigen comprised of a 110,000 dalton molecular weight glycoprotein on the surface of T lymphocyte cell populations inhuman blood comprised of CD4 and CD8 lymphocytes, said monoclonal antibody also binding to B cells and macrophages.

7. The monoclonal antibody of claim 6 which is produced by the cell line having the identifying characteristics of the cell line samples on deposit with the American Type Culture Collection and assigned A.T.C.C. No. HB 10297.

8. A monoclonal antibody which specifically binds to an antigen on the surface of T lymphocyte populations in human blood, said antigen being comprised of a 110,000 dalton molecular weight glycoprotein and being detectible on CD4 helpers inducer cells, but essentially undetectible on CD4 suppressor inducer cells.

9. A method of distinguishing between helper inducer and suppressor inducer cells in a sample of human CD4 lymphocyte populations comprising, contacting said sample with a monoclonal antibody identified as the IF7 monoclonal antibody for a time and under conditions sufficient for the formation of immunological complexes between said IF7 monoclonal antibody and CD4 helper inducer cells and then detecting said immunological complexes resulting from said contact between said monoclonal antibody and said cells in said sample, said cells complexed with said monoclonal antibody being CD4 helper inducer cells.

10. The method of claim 9 including the step of labelling said monoclonal antibody with a detectible compound prior to contacting said sample with said monoclonal antibody such that said complexes are labelled with said detectible compound as said complexes, if any, are formed upon contacting of said sample with said labelled monoclonal antibody.

11. The method of claim 9 including the step of separating the detected immunological complexes by cell sorting flow cytometric procedures.

12. The method of claim 10 in which said detectible compound is a fluorescent compound.

13. The method of claim 10 in which said detectible compound is an enzyme capable of producing a substrate reaction detectible compound.

14. A murine monoclonal antibody of the mouse IgG1 isotype which is specific for an antigen identified as the 1F7 antigen.

15. The monoclonal antibody of claim 14 in detectible labelled form.

16. The monoclonal antibody of claim 15 wherein said label is selected from the group consisting of a dye, a radioactive element and an electron dense element.

17. The monoclonal antibody of claim 14 attached to a compound selected from the group consisting of chemotherapeutic, photoactivated-toxic and radioactive agents.

18. A method of detecting and measuring 1F7 antigen in liquid biological samples of subsets of CD4 inducer lymphocytes comprising:
(a) contacting a liquid biological sample with 1F7 monoclonal antibody conjugated with a detector group selected from the group consisting of a fluorescent compound, a radioactive element and an enzyme;
(b) detecting and measuring the 1F7 antigen/antibody complex formed, if any, by use of a detecting and measuring means appropriate to the detector group selected, and
(c) determining the 1f7 present in said biological sample as the result of the detection and measurement of the complex of step (b).

19. The method of claim 18 including the step of flow cytometric cell sorting of an CD4 inducer lymphocytes bound by said conjugated monoclonal antibody.

20. A hybridoma cell line which produces a monoclonal antibody that binds to the antigen identified by the monoclonal antibody produced by the hybridoma cell line having A.T.C.C. Deposit No. HB 10297.

21. A monoclonal antibody which binds to the antigen identified by the monoclonal antibody produced by the hybridoma cell line having A.T.C.C. Deposit No. HB 10297.

* * * * *

UNITED STATES PATENT AND TRADEMARK OFFICE
CERTIFICATE OF CORRECTION

PATENT NO. : 5,120,642
DATED : June 9, 1992
INVENTOR(S) : Stuart F. Schlossman and Chikao Morimoto It is certified that error appears in the above-identified patent and that said Letters Patent is hereby corrected as shown below:

Column 1, line 49, change "ConcanaviIin" to --Concanavilin--.

Column 2, line 16, change "et aI." to --et al.--;

line 16, change "ImmunoI." to --Immunol.--.

Column 2, line 40, change "et aI." to --et al.--.

line 59, after "are" insert --expressed--;

line 62, change "CD4-CDw29" to --CD4+CDw29+--.

Column 3, line 10, change "recallantigen" to --recall antigen--;

line 10, change "are" to --as--;

line 12, change "nad" to --and--;

lines 15-16, change "insulture" to --in culture--;

line 27, change "desied" to --desired--.

UNITED STATES PATENT AND TRADEMARK OFFICE
CERTIFICATE OF CORRECTION

PATENT NO. : 5,120,642

DATED : June 9, 1992

INVENTOR(S) : Stuart F. Schlossman and Chikao Morimoto

It is certified that error appears in the above-identified patent and that said Letters Patent is hereby corrected as shown below:

Column 4, lines 11-12, change "monoclonaI" to

--monoclonal --;

line 31, change "CD4+1F7°" to --CF4+1F7+--.

line 59, change "asoites" to --ascites--.

Column 5, line 16, change "et aI. " to --et al.--;

line 19, change "CD8." to --CD8+"--;

line 21, change "Iysis" to --lysis--;

line 27, change "BI" to --B1--;

lines 43-44, change "helperinducer" to

--helper-inducer--;

line 50, change "IF7" to --1F7--;

line 63, change "54%+3%" to --54%±3%--.

UNITED STATES PATENT AND TRADEMARK OFFICE
CERTIFICATE OF CORRECTION

PATENT NO. : 5,120,642

DATED : June 9, 1992

INVENTOR(S) : Stuart F. Schlossman and Chikao Morimoto

It is certified that error appears in the above-identified patent and that said Letters Patent is hereby corrected as shown below:

Column 6, line 1, change "CD4" to --CD4+--;

line 16, change "ceIl" to --cell--;

line 17, change "fIuorescence" to --fluorescence--;

line 21, change "IF7+" to --1F7+--;

lines 24-25, change "fluoresce-inconjugated" to --fluorescein-conjugated--;

line 28, change "ImmunoI." to --Immunol.-- line 33, change "monoclonaI" to --monoclonal--;

line 66, change "IF7-" to --1F7- --;

line 67, change "IF7+" to --1F7+--;

UNITED STATES PATENT AND TRADEMARK OFFICE
CERTIFICATE OF CORRECTION

PATENT NO. : 5,120,642

DATED : June 9, 1992

INVENTOR(S) : Stuart F. Schlossman and Chikao Morimoto

It is certified that error appears in the above-identified patent and that said Letters Patent is hereby corrected as shown below:

Column 7, line 8, change "CD4,1F7-" to --CD4+1F7- --;

line 32, change "et aI." to --et al.-- line 33, change "et aI." to --et al.-- lines 37-38, after "However" insert a comma (,);

line 41, change "antilF7" to --anti-1F7--;

line 49, change "CD4+1F7+" to --CD4+1F7- --;

line 66, change "104)" to --$10^4$)--.

line 67, change "CD4+1F7-" to --CD4+1F7+--.

Column 8, line 11, change "CD4+1F7-" to --CD4+1F7+--;

line 23, change "ImmunoI." to --Immunol.--;

line 29, change "CD4+CDw29-" to --CD4+CDw29+--;

line 32, change "CD4+1F7-" to --CD4+1F7+--;

line 52, change "IF7" to --1F7--.

UNITED STATES PATENT AND TRADEMARK OFFICE
CERTIFICATE OF CORRECTION

PATENT NO. : 5,120,642
DATED : June 9, 1992
INVENTOR(S) : Stuart F. Schlossman and Chikao Morimoto It is certified that error appears in the above-identified patent and that said Letters Patent is hereby corrected as shown below:

Column 9, lines 38-39, change "(anti-TQI" to

--(anti-TQ$_1$--;

line 43, change "IF7" to --1F7--;

line 46, change "IF7" to --1F7--;

line 52, change "IF7" to --1F7--;

line 64, change "IgGI" to --IgG1--;

line 65, change "anti-TQ$_I$," to --anti-TQ$_1$--.

Column 10, line 13, change "ImmunoI." to --Immunol.--;

line 18, change "!F7" to --1F7--;

line 18, change "B-CeIl" to --B-cell--;

line 33, change "NaCI" to --NaCl--;

line 45, change "al ," to --al.,--;

line 47, change "Iysis" to --lysis--;

line 52, change "Iysis" to --lysis--;

line 53, change "HCI" to --HCl--.

UNITED STATES PATENT AND TRADEMARK OFFICE
CERTIFICATE OF CORRECTION

PATENT NO. : 5,120,642

DATED : June 9, 1992

INVENTOR(S) : Stuart F. Schlossman and Chikao Morimoto

It is certified that error appears in the above-identified patent and that said Letters Patent is hereby corrected as shown below:

Column 11, line 4, change "IF7 to --1F7--;

line 9, change "aI. ImmunoI." to

--al. Immunol.--;

line 10, change "Iysates" to --lysates--;

line 38, change "IF7" to --1F7--;

line 41, change "IF7" to --1F7--;

line 55, change "IF7" to --1F7--;

line 63, change "Tal" to --$Ta_1$--.

Column 12, line 36, change "IF7" to --1F7--;

line 57, change "Tal" to --$Ta_1$--;

line 67, change "IF7" to --1F7--.

UNITED STATES PATENT AND TRADEMARK OFFICE
CERTIFICATE OF CORRECTION

PATENT NO. : 5,120,642

DATED : June 9, 1992

INVENTOR(S) : Stuart F. Schlossman and Chikao Morimoto

It is certified that error appears in the above-identified patent and that said Letters Patent is hereby corrected as shown below:

Column 13, line 1, change "Tal" to --$Ta_1$--;

line 7, change "$Ta_1+$" to --$Ta_1+$--;

line 9, change "aI." to --al.--;

line 11, change "$Ta_1+$" to --$Ta_1+$--;

line 12, change "IF7+" to --1F7+--;

line 16, change "$Ta_1+$" to --$Ta_1+$--;

line 18, change "$Ta_1$" to --$Ta_1$--;

line 33, change "1F" to --1F7--;

line 35, change "Tal" to --$Ta_1$--;

line 56, change "CD4*UCHL-1+" to --CD4+UCHL-1+--.

Column 14, line 4, change "IF7" to --1F7--.

line 5, change "CD4." to --CD4+--;

line 43, change "inhuman" to --in human--;

line 57, change "helpers" to --helper--.

UNITED STATES PATENT AND TRADEMARK OFFICE
CERTIFICATE OF CORRECTION

PATENT NO. : 5,120,642
DATED : June 9, 1992
INVENTOR(S) : Stuart F. Schlossman and Chikao Morimoto It is certified that error appears in the above-identified patent and that said Letters Patent is hereby corrected as shown below:

Column 16, line 15, change "1f7" to --1F7--;

line 19, change "an" to --the--.

Signed and Sealed this

Tenth Day of May, 1994

Attest:

BRUCE LEHMAN

Attesting Officer

Commissioner of Patents and Trademarks